(12) United States Patent
Little, Jr.

(10) Patent No.: US 9,989,359 B2
(45) Date of Patent: Jun. 5, 2018

(54) NONDESTRUCTIVE, ABSOLUTE DETERMINATION OF THICKNESS OF OR DEPTH IN DIELECTRIC MATERIALS

(71) Applicant: Evisive, Inc., Baton Rouge, LA (US)

(72) Inventor: Jack R. Little, Jr., Baton Rouge, LA (US)

(73) Assignee: Evisive, Inc., Baton Rouge, LA (US)

( * ) Notice: Subject to any disclaimer, the term of this patent is extended or adjusted under 35 U.S.C. 154(b) by 0 days. days.

(21) Appl. No.: 15/023,297

(22) PCT Filed: Sep. 22, 2014

(86) PCT No.: PCT/US2014/056730
§ 371 (c)(1),
(2) Date: Mar. 18, 2016

(87) PCT Pub. No.: WO2015/047931
PCT Pub. Date: Apr. 2, 2015

(65) Prior Publication Data
US 2016/0298957 A1  Oct. 13, 2016

Related U.S. Application Data

(60) Provisional application No. 61/882,288, filed on Sep. 25, 2013.

(51) Int. Cl.
*G01R 27/04* (2006.01)
*G01B 15/02* (2006.01)
(Continued)

(52) U.S. Cl.
CPC ............. *G01B 15/02* (2013.01); *G01N 22/00* (2013.01); *G01N 22/02* (2013.01)

(58) Field of Classification Search
CPC ......... G01B 15/02; G01N 22/00; G01N 22/02
(Continued)

(56) References Cited

U.S. PATENT DOCUMENTS

| 2,299,982 A | 9/1961 | Broussaud ................... 324/58.5 |
| 3,025,463 A | 3/1962 | Emanuel et al. ............ 324/58.5 |

(Continued)

FOREIGN PATENT DOCUMENTS

| GB | 2121563 | 2/1984 |
| JP | 61274209 | 4/1986 |

(Continued)

OTHER PUBLICATIONS

Bahr, A., Microwave Nondestructive Testing Methods (1982).
(Continued)

*Primary Examiner* — Farhana Hoque
(74) *Attorney, Agent, or Firm* — John H. Runnels

(57) ABSTRACT

Enhanced measurement of thickness in bulk dielectric materials is disclosed. Microwave radiation is partially reflected at interfaces where the dielectric constant changes (e.g., the back wall of a part). The reflected microwaves are combined with a portion of the outgoing beam at each of at least two separate detectors. A pair of sinusoidal or quasi-sinusoidal waves results. Thickness or depth measurement is enhanced by exploiting the phase and amplitude relationships between multiple sinusoidal or quasi-sinusoidal standing waves at detectors sharing a common microwave source. These relationships are used to determine an unambiguous relationship between the signal and the thickness or depth.

19 Claims, 7 Drawing Sheets

(51) Int. Cl.
  *G01N 22/00* (2006.01)
  *G01N 22/02* (2006.01)
(58) Field of Classification Search
  USPC .................................. 324/637, 642, 644
  See application file for complete search history.

(56) References Cited

U.S. PATENT DOCUMENTS

| | | | |
|---|---|---|---|
| 3,144,601 A | 8/1964 | Slabodsky | 324/58.5 |
| 3,271,668 A | 9/1966 | Claus et al. | 324/58.5 |
| 3,278,841 A | 10/1966 | Hanson et al. | 324/58.5 |
| 4,087,746 A | 5/1978 | Kanae | 324/58.5 |
| 4,123,703 A | 10/1978 | Robinson | 324/58.5 |
| 4,274,288 A | 6/1981 | Tittmann et al. | 73/602 |
| 4,344,030 A | 10/1982 | Anderson et al. | 324/999 |
| 4,470,123 A | 9/1984 | Magenheim et al. | 364/563 |
| 4,514,680 A | 4/1985 | Heikkila et al. | 324/999 |
| 4,520,308 A | 5/1985 | Rohde et al. | 324/58.5 |
| 4,581,574 A | 4/1986 | Goodman et al. | 324/58 |
| 4,707,652 A | 11/1987 | Lowitz | 324/631 |
| 4,754,214 A | 6/1988 | Bramanti et al. | 324/999 |
| 5,216,372 A | 1/1993 | Zoughi et al. | 324/644 |
| 5,384,543 A | 1/1995 | Bible et al. | 324/644 |
| 5,539,322 A | 7/1996 | Zoughi et al. | 324/644 |
| 5,574,379 A | 11/1996 | Darling, Jr. | 324/642 |
| 6,005,397 A | 12/1999 | Zoughi et al. | 324/644 |
| 6,172,510 B1 | 1/2001 | Liu | 324/632 |
| 6,359,446 B1 | 3/2002 | Little, Jr. | 324/637 |
| 6,653,847 B2 | 11/2003 | Little, Jr. | 324/637 |
| 7,190,177 B2 | 3/2007 | Zoughi et al. | 324/642 |
| 7,777,499 B2 | 8/2010 | Little, Jr. | 324/637 |
| 8,035,400 B2 | 10/2011 | Little, Jr. | 324/637 |
| 2005/0088776 A1* | 4/2005 | Saliba | G11B 5/584 360/77.12 |
| 2010/0283483 A1* | 11/2010 | Little, Jr. | G01N 22/00 324/642 |

FOREIGN PATENT DOCUMENTS

| | | |
|---|---|---|
| SU | 1350570 | 11/1987 |
| WO | WO 1997010514 A1 | 3/1997 |
| WO | WO 2004/111572 | 12/2004 |

OTHER PUBLICATIONS

Ganchev, S. et al., "Microwave detection of defects in glass reinforced polymer composites," Proc. SPIE—International Society for Optical Engineering USA, vol. 2275, pp. 11-20 (1994).

Howell, C. et al., The use of low cost industrial AM-CW 'Microwave Distance Sensors' for industrial control applications (no date).

Khanfar, A. et al., "Microwave near-field nondestructive detection and characterization and disbands in concrete structures using fuzzy logic techniques," Composite Structures Elsevier UK, vol. 62, pp. 335-339 (2003).

Kurian, J. et al., "Microwave non-destructive flaw/defect detection system for non-metallic media supported by mirroprocessor-based instrumentation," J. of Microwave Power and Electromagnetic Energy, vol. 24, pp. 74-78 (1989).

Lucian, A. et al., "The development of microwave NDT technology for the inspection of nonmetallic materials and composites," Proceedings of the Sixth Symposium on Nondestructive Evaluation of Aerospace and Weapons Systems Components and Materials, pp. 199-232 (San Antonio, TX 1967).

* cited by examiner

NONDESTRUCTIVE, ABSOLUTE DETERMINATION OF THICKNESS OF OR DEPTH IN DIELECTRIC MATERIALS

This is the United States national stage of international application PCT/US2014/056730, international filing date Sep. 22, 2014, which claims the benefit of the Sep. 25, 2013 filing date of U.S. provisional patent application Ser. No. 61/882,288 under 35 U.S.C. § 119(e). The complete disclosure of priority application 61/882,288 is hereby incorporated by reference in its entirety.

This invention was made with government support under contract numbers FA865008C5306 and FA865012C5109 awarded by the United States Department of Defense (United States Air Force). The United States Government has certain rights in this invention.

TECHNICAL FIELD

This invention pertains to an apparatus and method for the non-destructive determination of the depth of features in a dielectric material, the thickness of a dielectric material, and the use of thickness information so determined in nondestructive evaluation (NDE) of bulk dielectric materials.

BACKGROUND ART

There is an unfilled need for improved, nondestructive means to test bulk dielectric materials for flaws, defects, irregularities, and other features; and particularly to determine the absolute thickness of bulk dielectric materials when given access to only one side of a part under inspection. Additionally, there is an unfilled need for improved, nondestructive means to determine variations in the density (or porosity) when the thickness of a bulk dielectric material is known. For example, there is an unfilled need for improved, nondestructive means for examining dielectric materials in three dimensions, volumetrically, and measuring both thickness and changes in thickness. For a manufactured dielectric component that has been in service for some time, the remaining thickness is often important as an indicator of the component's remaining life; but it can be difficult to measure thickness when only one surface of the component is accessible. Density can also be a major indicator of the serviceability of manufactured dielectric components, because the density often relates directly to the strength of the component. The dimensions of a manufactured part are often known or are easily measured, but it is more difficult to determine density and variations in density. There is an unfilled need for improved means for the nondestructive determination of density and changes in density of a bulk dielectric material when its thickness is known.

For example, there is an unfilled need for enhanced, nondestructive means for measuring the remaining wall thickness in dielectric tanks and pipes. (This invention has numerous applications, and is not limited to the inspection of tanks and pipes.)

Modern chemical processing often involves the use of components made of dielectric materials. Common dielectric material product forms include fiber reinforced plastic (often called "fiberglass" or "FRP") pipes and vessels. These materials are also commonly used in modern infrastructure, such as drinking water and waste water processing. There exists an unfilled need for improved means to measure the thickness of such materials nondestructively, especially for means that may be employed while the produce remains in-service, and where there is access to only one side of the dielectric component. (This invention has numerous applications, and is not limited to the inspection of FRP.)

Due to the corrosive or abrasive nature of the fluids that are often used in various processes, the wall thickness often diminishes over time as a direct result of service-induced degradation. These service-induced thickness changes are difficult to detect nondestructively through conventional means.

It is highly desirable that a testing method should be nondestructive, and that it should be usable whether a facility is running or idle. Furthermore, because the access space outside the component can be limited, and the geometry of a component can be complex, any portion of the detection machinery that must be in contact with the component (or in the vicinity of the component) should be small enough to accommodate the available space and geometry.

When the component to be tested is made of metal, then well-established ultrasonic inspection techniques can be used. However, ultrasonic inspection cannot be used effectively for reinforced dielectric materials, because the structural fibers scatter nearly all sound energy, and return little usable signal. The mesh or fabric of a composite material so strongly scatters and disperses ultrasonic waves that the resulting reflection is extremely noisy. Eddy current measurements or magnetic measurements do not work well in these materials either, because they do not conduct electricity.

Neither is radiography particularly helpful. X-ray radiography can be used to detect changes in bulk density or to detect changes in thickness, but it requires access to both sides of the component under inspection. This renders X-ray radiography ineffective for in-service inspection of many components.

Another example of an unfilled need for improved methods to measure density lies in the field of engineered ceramic composites. In such composites both the reinforcing fibers and the matrix are made of a ceramic material. Typically, the fibers are woven or otherwise arranged into a support structure into which the matrix is deposited by chemical methods. The matrix is typically deposited iteratively. The chemical reaction that results in the deposition occurs in sequential steps, with each step depositing additional ceramic material into the interstices between reinforcing fibers. Since the location of the fibers and the outer boundary of the part do not change, the porosity of the part decreases (and its density correspondingly increases) with each iteration. When the parts are highly engineered and their physical dimensions are closely controlled, the physical thickness, measured in inches or mm, is generally known within close tolerances. Because the strength of a part is typically a function of its density, it would be highly desirable to have improved nondestructive means to measure density. Ultrasonic methods are not effective for determining density in such materials, due to the scattering of sound waves by the reinforcing fibers. Neither can eddy current or magnetic methods be used, as the ceramic composites are bulk nonconductors. Although changes in density can be detected by radiography, the changes of interest in ceramic composite applications are typically too small to be resolved by conventional radiography. Additionally, radiography requires access to both sides of the part, for that reason is not an acceptable method in many circumstances.

An overview of microwave testing techniques is given in A. Bahr, *Microwave Nondestructive Testing Methods* (1982).

Several microwave nondestructive testing techniques are disclosed in A. Lucian et al., "The Development of Microwave NDT Technology for the Inspection of Nonmetallic Materials and Composites," pp. 199-232 in *Proceedings of the Sixth Symposium on Nondestructive Evaluation of Aerospace and Weapons Systems Components and Materials* (San Antonio, Tex. 1967).

J. Kurian et al., "Microwave Non-Destructive Flaw/Defect Detection System for Non-Metallic Media Supported by Microprocessor-Based Instrumentation," *J. Microwave Power and Electromagnetic Energy*, vol. 24, pp. 74-78 (1989) discloses a method for detecting defects in a tire by measuring transmission of microwaves from a dipole transmitting antenna inside the tire, through the treads of the tire, with transmission detected by a linear array of detectors. Differential rates of transmission were correlated with changes in thickness or with defects.

C. Howell et al., *The Use of Low Cost Industrial AM-CW 'Microwave Distance Sensors' for Industrial Control Applications* (no date) discloses a microwave distance sensor to measure distances to an object from about 15 centimeters to about 6 meters away, by measuring the phase angle of a returned amplitude-modulated microwave signal reflected from the object.

U.S. Pat. No. 3,278,841 discloses a microwave flaw detection system, particularly for use with large, solid-propellant rocket motors. Microwaves were transmitted from inside the propellant, reflected off a metal casing, and detected by a receiver displaced from the microwave transmitter. Irregularities in the strength of the received signal were correlated with cracks or other flaws in the propellant.

U.S. Pat. No. 4,520,308 discloses a system for measuring the thickness of a dielectric material by measuring the phase shift of microwaves transmitted along a microwave strip line conductor adjacent to the material whose thickness is being measured. See also U.S. Pat. No. 4,123,703.

U.S. Pat. No. 2,999,982 discloses a Doppler-effect-based method for microwave detection of inhomogeneities in compact materials such as polished glass. Relatively high scanning speeds were used to produce a Doppler effect. In the one example given, the relative speed of the glass versus the detector was 650 centimeters per second.

U.S. Pat. No. 3,144,601 discloses a method for microwave detection of inhomogeneities in non-conducting materials such as glass sheets and plates. Detection was performed by simple measurement of the echoes of the reflected microwaves; by measuring losses in intensity following transmission through the object; or by mixing incident and reflected waves to create beats, particularly when the material being examined was traveling (i.e., detecting Doppler shifts in the frequency of the reflected microwaves).

U.S. Pat. No. 3,271,668 discloses the use of microwaves to measure the rate of progressive attrition from a surface of a body of a solid dielectric material; for example, measuring the burning profile in a solid rocket motor. Microwaves were transmitted through the fuel (or other material), the surface of which reflected some of the microwaves back to a detector. The relative phase of incident and reflected microwaves varied as the distance from the microwave transmitter to the surface of the burning fuel changed, allowing the distance to the surface of the fuel to be determined as a function of time.

U.S. Pat. No. 4,707,652 discloses a technique for detecting impurities in a bulk material by measuring changes in the scattering of microwave radiation incident on the bulk material.

U.S. Pat. No. 4,514,680 discloses a method for detecting knots in lumber, by transmitting microwaves through the lumber from two sources of the same intensity, but with a 180-degree phase shift. Transmitted microwaves are detected on the opposite side of the lumber. If the lumber is knot-free, there is a null in the microwave field at the detectors, but if a knot is present the phase and amplitude of microwave radiation at the detectors are altered.

U.S. Pat. No. 4,581,574 discloses a method for determining the average dielectric constant of a dielectric material having a conductive surface, by transmitting microwaves from two transducers into a sheet of the material, and making measurements of the energies of reflected microwaves. By measuring average dielectric constants along a plurality of paths in the plane of the sheet, locations of variations within the sheet may be identified.

U.S. Pat. No. 4,274,288 discloses an acoustic, interferometric method for measuring the depth of a surface flaw such as a crack.

U.S. Pat. No. 4,087,746 discloses a method for determining optical anisotropy in a dielectric material by measuring changes in the polarization of microwaves transmitted through the material.

U.S. Pat. No. 6,172,510 discloses the probing of targeted portions of a layered material by microwave radiation focused onto the targeted portion by adjustment of antenna position and orientation establishing a single oblique incidence path for reflection of antenna emitted probing radiation. Signal measurements of the radiation along the oblique incidence path are obtained to provide for evaluation and detection of defects in the targeted portion of the structure being probed.

A. Khanfar et al., "Microwave near-field nondestructive detection and characterization and disbands in concrete structures using fuzzy logic techniques," *Composite Structures Elsevier UK*, vol. 62, pp. 335-339 (2003) discloses a near-field microwave nondestructive testing technique for disbond/crack detection and evaluation in a concrete structure. The frequency of operation and standoff distance could be optimized to achieve maximum sensitivity to the presence of a disband, which is viewed as an additional layer and which changes the properties of the effective reflection coefficient (phase and magnitude). The change depends on the thickness and location of the disbond. Multiple frequency measurements could be used to obtain disbond location and thickness information. A fuzzy logic model was described relating the phase of reflection coefficient, frequency of operation, and standoff distance to the disbond thickness and depth.

S. Ganchev et al., "Microwave detection of defects in glass reinforced polymer composites," *Proc. SPIE —International Society for Optical Engineering USA*, vol. 2275, pp. 11-20 (1994) discloses the use of microwaves for defect and flaw detection in glass reinforced polymer composites. The standoff distance and the frequency were studied as means of increasing detection sensitivity.

A prior microwave method for the nondestructive testing of dielectric components employs virtual standing waves. See U.S. Pat. Nos. 6,359,446, 7,777,499, 6,653,847, and 8,035,400 These methods, while effective for detecting and characterizing thickness or density changes over a small range (plus or minus ¼ of the wavelength "λ" in the material being inspected), can give ambiguous results in some circumstances. Several different values for the thickness or density can correspond to a single value of the measured output. Despite the improvements represented by these earlier methods, the U.S. Pat. No. 8,035,400 patent frankly acknowledged: "There can be ambiguity in interpreting an interferometric signal, as points within the specimen that are spaced an integral number of half-wavelengths apart may not initially be distinguished from one another, due to the identical phase of the waves reflected from such points (where the wavelength in question is that within the material, which generally differ from the wavelength in air or vacuum, depending on the index of refraction)." One solution proposed was that "if a frequency is chosen to reduce the number of wavelengths needed to traverse the thickness of the specimen, one may enhance the sensitivity at a selected depth range with minimal ambiguity. In the special case where the specimen thickness is less than (preferably substantially less than) half the wavelength, then the imaging may be optimized for a single, very narrow band of the thickness within the specimen." However, no solution was proposed for the more general problem of resolving these ambiguities when the thickness of the specimen can be several multiples of a wavelength. There is an unfilled need for improved testing methods that can resolve such ambiguities in measurements of bulk dielectric thickness, density, or features.

See also U.S. Pat. Nos. 5,539,322, 5,574,379, 5,216,372, 6,005,397, 3,025,463, 4,344,030, 4,754,214, 5,384,543, 7,190,177; Japanese patent abstract 61274209; and published international application WO9710514.

DISCLOSURE OF INVENTION

I have discovered an improved high resolution method and apparatus to determine depth and thickness in bulk dielectric materials. I have discovered a novel way to resolve the ambiguity in depth or thickness that was left unresolved in earlier interferometry-based nondestructive measurement techniques. The novel method can unambiguously resolve depth and thickness with high precision. Monochromatic radiation, preferably microwave radiation, more preferably microwaves in the 5-50 gigahertz frequency range, is used to interrogate a sample. The microwaves are partly reflected at each feature where the dielectric constant changes (e.g., to measure thickness changes as the microwave beam encounters the back wall of the specimen under inspection, with varying distance between the back wall of the specimen and the microwave source and detectors). In a preferred embodiment, the apparatus comprises a single microwave source, and two or more detectors. The distance(s) between the detectors (and therefore their phase relationship) is known (or can be measured). A portion of the transmitted beam is combined with the signal reflected by the specimen under inspection. These two signals have the same frequency, but may differ in amplitude and phase. The signals combine at the location of each detector to produce an interference pattern, a pattern that changes as the thickness of the specimen changes, or as the position of the specimen changes relative to the detector. For each detector, the interrogating radiation may be thought of as a sinusoidal (or quasi-sinusoidal) standing wave. If one used only a single detector, then the relationship between the detector output and the sample thickness would produce ambiguous thickness measurements, with identical output values occurring every ¼ wavelength in thickness (or $\lambda/4$) as the thickness changes (assuming that all other parameters remained unchanged). Simply repeating the measurements with multiple detectors does not resolve the ambiguity, regardless of the spacing of the detectors (whether spacing is measured in distance or in phase).

As used in the specification and claims, unless context clearly indicates otherwise, terms such as "thickness," "depth," and the like should be understood as referring in the first instance to distance as measured in units of the wavelength ($\lambda$) of the microwave energy that is used to perform the inspection, where the wavelength is the effective wavelength in the material under inspection, which in general will differ from the wavelength in air (or vacuum). Conversion to other convenient units (e.g., mm, cm, in) may easily be performed where desired. Fundamentally, an initial determination in accordance with the present invention determines the number of unit wavelengths in the material being inspected, with conversion into measurements in other units being secondary or derived from the number of wavelengths thus determined.

I have discovered a method of "combining" the output of multiple detectors into a novel phase plot, a phase plot that can resolve the ambiguity that is otherwise inherent in measurements of thickness, depth, etc. A simple example will illustrate: Consider an embodiment with two detectors spaced $\lambda/4$ apart (based on $\lambda$ in air). (The technique can be generalized to detector numbers greater than two, and to detector spacings other than $\lambda/4$. In general, increasing the number of detectors will improve resolution.) For the purposes of this illustration, the distance between the microwave source (and detectors) to the front surface of the specimen will be held constant. Thus the phase relationship between the front surface and the detectors is constant. Additionally, the contribution of the front surface reflection to the signal at each detector remains constant in both phase and amplitude, even as the thickness varies. The output signals from the two detectors vary periodically in the thickness domain, either sinusoidally or quasi-sinusoidally. For an individual detector, this periodic behavior produces an ambiguity in the inferred thickness. The present invention allows this ambiguity to be resolved. It is preferred that the spacing between the two detectors be chosen so that the absolute value of one detector's output is a maximum when the output of the other detector is halfway between its own maximum and minimum. (This point may or may not be equal to zero, depending on where the null is set in a particular case.) Alternatively, it is preferred that the spacing between two detectors be chosen so that the absolute value of the slope of a line tangent to the standing wave is a maximum on one detector when the slope of a line tangent to the standing wave for the other detector is zero. To illustrate, in a hypothetical ideal case where the output signal is precisely sinusoidal, the preferred spacing between the detectors would be such that the phase difference between the two detectors is 90°+(n×180°), where n is an integer (which may be positive, negative, or zero).

When the output signals of the two detectors are plotted against one another (not necessarily as a direct function of time, nor necessarily as a direct function of distance, but against one another)—for example with the voltage at the "A" detector as the "X" value and the voltage at the "B" detector as the corresponding "Y" value in an (X,Y) data pair—then the resulting plot will generally be an ellipse (or quasi-ellipse), as depicted schematically in FIG. 1. (The ellipse could even be a circle if the relative sensitivities of the two detector outputs were identical.) Each time the thickness of the material changes by ½λ, the (X,Y) data point repeats and passes around the ellipse. This combination of the output from two detectors extends the unambiguous range for measuring thickness by a factor of 2, from ¼λ to ½λ. If a straight line is drawn from any point on the ellipse to the center, the angle from that line to the x-axis (or any other fixed line passing through the origin) corresponds to the thickness within a range of ½λ.

Actually, the idealized elliptical phase plot shown in FIG. 1 is oversimplified since it disregards the loss of microwave energy that also occurs with changes in thickness. For a particular type of dielectric material, the attenuation increases as a function of sample thickness. As depicted in FIG. 2, the attenuation losses convert the theoretically lossless phase plane ellipse of FIG. 1 into something more similar to an elliptical spiral. These losses actually are beneficial for the measurement process, because they provide additional information that can be extracted. In the phase plane spiral of FIG. 2, note that the values of (X,Y) do not repeat. The phase plane spiral curve does not cross itself, meaning that the periodic ambiguity in thickness depicted in FIG. 1, which exists when only the relative phase of multiple detectors is considered, is eliminated by plotting the (X,Y) coordinates represented by the signal from the multiple detectors in phase plane space, with the amplitude of the signal decreasing with increasing sample thickness. (Actually, as shown in FIG. 5 of Appendix A of priority application 61/882,288, even with the novel phase plane analysis there can still sometimes be regions of ambiguity arising from internal reflections of microwaves from boundaries. Even when such complications exist, most measurements in the phase plane analysis still produce unambiguous determinations of thickness/depth.)

Apparent changes in thickness, measured in units of the microwave wavelength in the material, can result either from actual changes in dimension (e.g., measured in inches or centimeters), or from density changes (which cause changes in refractive index and therefore wavelength). Unless context clearly indicates otherwise, as used in this disclosure and in the Claims, the term "thickness" should be understood to refer to the apparent thickness of a material, as measured in units of wavelength of the interrogating radiation. In other words, the "thickness" is the apparent thickness, which can be a function both of the actual dimensions of an object, and its density and refractive index, which may vary as a function of position. The invention provides an apparatus and method for the non-destructive determination of specimen thickness (or feature depth), measured in units of wavelength within the inspected material, and the use of thickness information so determined in nondestructive evaluation (NDE) of bulk dielectric materials. The refractive index of a material depends on its chemical composition. The refractive index also varies as a function of the density, even with a constant chemical composition. The dependence of refractive index upon density results in a change in the wavelength of the electromagnetic energy as it propagates through regions of varying density. Thus the ability to determine changes in the position of a standing electromagnetic wave in a specimen, the dimensions of which are known, permits determination of the refractive index, and hence the density (or porosity, which is inversely related to the density).

The detector may be scanned relative to the specimen at any desired speed, and the scanning speed need not even be uniform. The novel detection technique is not based on Doppler-shifts in frequency, which result from motion, but rather is based on interference between reflected and reference microwaves that have substantially the same frequency, where the interference is caused by changes in location (independent of motion per se).

The novel technique can detect thickness changes and changes in dielectric constant (which in dielectrics may, for example, result from changes in density or porosity), in essentially any dielectric materials. The technique can also be successfully used on composite materials containing conductive components, but whose construction makes them overall nonconductors—for example, carbon fiber composites.

The novel method and apparatus have been successfully tested in a prototype embodiment. The microwave transmitter/detector was small, and readily suited for use in environments in which access space may be limited.

The computed thickness value from the processed signal (from the detectors) may be plotted as "Z" in a 3-dimensional plot, where "X" and "Y" are Cartesian coordinates on the surface of a specimen, to produce a map of thickness. (Other coordinate systems may also be used in lieu of an orthogonal Cartesian system, as convenient for the shape of the particular specimen being inspected, for example cylindrical coordinates, toroidal coordinates, spherical polar coordinates, etc.) In an alternative embodiment, a fourth dimension may be added to a plot, using color palette variations to indicate the presence of defects in the specimen.

If desired, one may determine whether a through-thickness inspection is feasible for a particular specimen with a particular transducer by placing the transducer against one surface of the specimen and moving an object on the far side of the specimen. If the microwave energy fully penetrates the specimen, a change in the position of the object on the far side of the specimen should produce changes in the observed transducer signal. In such a case, a thickness measurement should be possible.

MODES FOR CARRYING OUT THE INVENTION

Substances such as fiberglass that produce noisy reflection patterns in ultrasonic techniques may be inspected at low noise levels with the novel microwave technique. For example, the novel technique readily detects thickness changes in fiberglass, or in ceramic composites.

There are many potential fields of use for the invention. As one illustration, the invention may be used to inspect fiber-reinforced plastic (FRP) pipe. Commercially available FRP pipe is a complex composite structure, typically containing many layers of varying composition, density, and dielectric constant. When microwaves are directed towards an FRP pipe, reflections return from all interfaces between materials of different dielectric constant. The returning signal is a superposition of many different waveforms, essentially identical in frequency, but generally differing in phase and amplitude. In general, the full thickness of the material is inspected, and all interfaces upon which the microwaves impinge contribute to the returning waveform. The present invention is capable of measuring the remaining thickness in such materials with a high degree of precision, accuracy, and repeatability.

Mixing a portion of the outgoing radiation with the reflected waveform results in a complex standing waveform. (The waveform is "standing," i.e., unvarying, similar to a vibrating string, so long as the relative positions of the transducer and the specimen remain unchanged, but in general it will vary as those positions vary.) The standing waveform that corresponds to a single detector passes from the inspection device (transducer), then usually through an intervening medium such as air, and then into the specimen. As the waveform passes through components of the specimen having differing indices of refraction, the wavelength changes, while the frequency remains constant. The higher the index of refraction, the slower the propagation of electromagnetic energy, and the shorter the wavelength becomes.

The present invention is capable of determining thickness unambiguously, using a combination of phase and amplitude measured by multiple detectors when the specimen is irradiated from a common microwave source.

Figure 7:
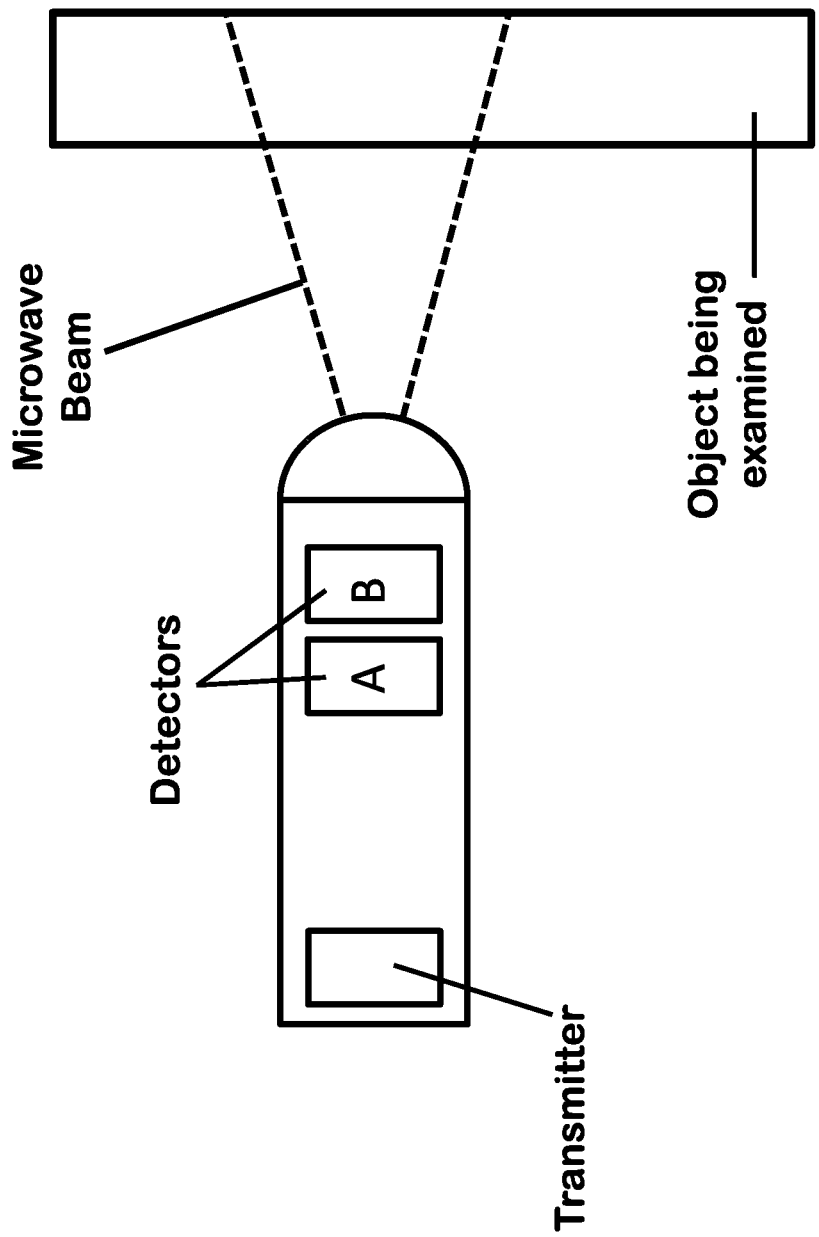
FIG. 7 depicts schematically a prototype embodiment of an apparatus in accordance with the present invention.

FIG. 7 depicts schematically a prototype embodiment of an apparatus in accordance with the present invention. The prototype apparatus comprised a transducer with a single microwave source (transmitter) and two detectors. The detectors output two channels of SIGNAL information (not shown). The detectors were separated by approximately 0.12 inch (0.30 cm) in the direction of propagation, corresponding to approximately ¼ wavelength. The SIGNALs from the two detectors were transferred to signal conditioning electronics, where they were amplified, filtered, and conditioned prior to being sent to an analog-to-digital converter (ADC). There were two position encoders, "X-Pos" and "Y-Pos" (not shown), the outputs of which were also sent to the ADC. The ADC transmitted digital data, containing SIGNAL information for both channels, and X and Y location data, to a processing computer, which then created images for chosen regions of interest.

In the prototype apparatus, the output voltage from the 2 separate detectors was combined in a display and analysis computer. In future embodiments, this data processing will be performed in a dedicated processor located on the transducer itself.

Figure 6:
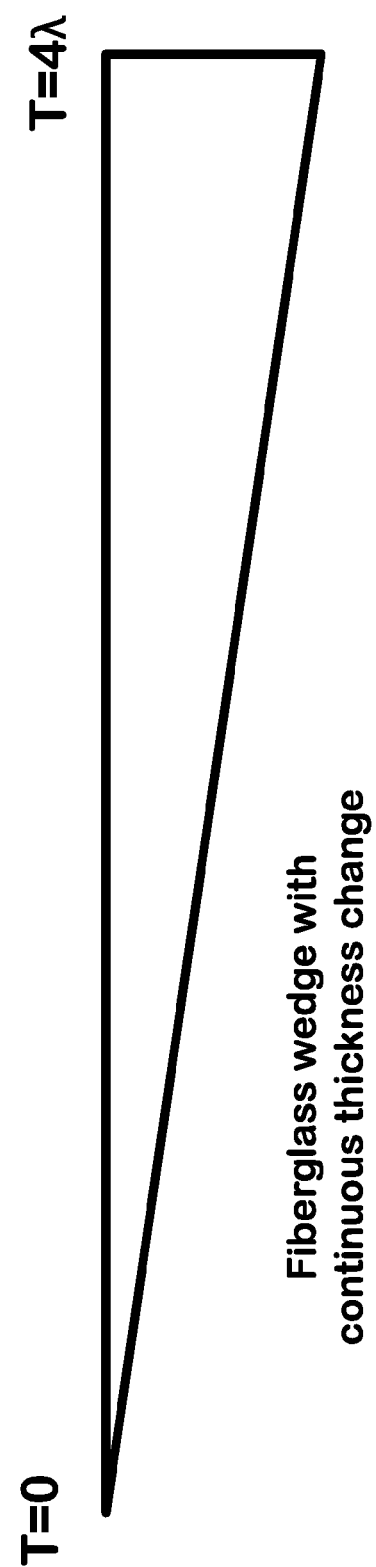
FIG. 6 depicts schematically, in cross section, a fiberglass wedge that was used for testing the prototype embodiment over a range of depths.

A fiberglass wedge was constructed for prototype testing; a cross section is illustrated schematically in FIG. 6. The wedge was scanned to confirm that acceptable data could be collected, and that the prototype embodiment worked as expected.

The Transducer

A preferred transducer was a microwave transceiver based on a Gunn diode. See, e.g., B. Hale (ed.), *The 1989 ARRL Handbook for the Radio Amateur*, pp. 32-57 & 32-58 (66th ed., 1988); *The Microwave Gunnplexer: An Introduction* (various authors, no date); M/A-COM Semiconductor Products, *Varactor Tuned Gunnplexer Transceiver "Front End"* (1985); Microwave Associates, *Varactor Tuned Gunn Oscillator Transceivers for Commercial Applications* (1977). The transducers that were used in prototype embodiments of the invention were tunable 10, 25, or 35 gigahertz transceivers (frequencies could be higher or lower if desired, e.g., 5-50 GHz). The transceiver could be used with or without a waveguide section. The detector had two microwave frequency diodes incorporated as part of the assembly. The detector diodes were located inside the outgoing radiation beam, between the aperture and the front surface of the transducer housing. The transducer was frequency-stable, and required only a 5-10 Volt DC power supply to produce the desired microwave output energies. It was mounted in a housing, which could either be moved by hand, or in future embodiments will preferably be moved by an automated inspection device (a robot).

The transducer included mechanical means to control the stand-off distance; the stand-off distance is preferably held constant. The transducer was connected to signal processing electronics, data acquisition hardware, and an imaging and analysis computer via a multiple-conductor cable.

The transducer was also connected to a position-encoder system for determining the X and Y position of the transducer. The position encoder outputs were fed to the computer for use in imaging and analysis of the specimen.

Signal Processing and Power Supply

In the prototype embodiment, the detection diodes were located at fixed positions within the path of the outgoing microwave beam, so that the output signal maintained a constant amplitude and frequency as seen by each detection diode. Alternatively, the positions of the detection diodes could be made variable, independent of varying the stand-off distance. Microwaves radiated from the transducer to the specimen being tested. Each time the microwave beam came to an interface between materials of different dielectric constants (e.g., the interface between air and the specimen, or the interface between the bulk specimen and a flaw or feature within it), a portion of the microwave energy was transmitted, and a portion was reflected. The portion that was reflected depended on the angle of incidence, the difference in the dielectric constants between the materials (which is related to the index of refraction), the surface texture, and other factors. Some of the reflected portion of the interrogating beam returned to the transducer, where it was detected by the detector diode(s). The reflected signal and the transmitted signal were of identical frequency, but (in general) differed in both amplitude and phase. These simple sinusoids or quasi-sinusoids added together (were mixed) at the detecting diode(s), to produce a DC voltage that changed as the sample (or portion of sample) under inspection changed. In most specimens there are many interfaces, producing many reflected signals. However, regardless of the complexity of the reflected signal, the detector diode(s) output produced a constant DC voltage when the position of the transducer relative to the specimen and the interrogating frequency were both held constant. This constant DC voltage is sometimes referred to as the "SIGNAL." The "SIGNAL" may comprise multiple components, from multiple detectors.

The SIGNAL was transferred to signal processing electronics via a wired connection. The observed SIGNAL was typically on the order of 1-100 millivolts at the input of the signal processing electronics. The SIGNAL was converted from analog to digital form by the data acquisition system described earlier. The analog SIGNAL was digitized for maximum resolution of the SIGNAL voltage.

Routing the SIGNAL directly to the data acquisition system would have diminished the resolution for extremely small defects that the intrinsic frequency stability and low noise of the transducer would otherwise permit. An amplifier was therefore included in the signal processing components, prior to the ADC. The amplifier improved SIGNAL resolution by a factor greater than 100, while maintaining an acceptable signal-to-noise ratio.

The data acquisition system supported eight differentially-connected analog input channels, each with its own negative signal connection. At least two analog channels were used to input amplified SIGNAL. Additional digital channels were used for input from the X and Y position encoders. In general, it is preferred to collect position information for both the X and Y positions of the transducer. However, it sometimes suffices to collect position information from a single position encoder. For example, when collecting data for a specimen having the shape of a right circular cylinder, the transducer may revolve radially around the cylinder while progressing axially down the cylinder at a known rate. Then the Y position is a direct function of the X position, and a single position encoder may suffice.

When the data from a scan over multiple locations is displayed graphically at an appropriate scale, the resulting image shows thickness changes in the specimen. Typically, the collected dataset contains far more detail than is conveniently represented in a single image. The regions of interest are therefore selected, and an image is created by changing the scale and color (or gray scale) gradient for the SIGNAL for a clear visual display of the features of interest. The stand-off spacing is selected to obtain the depth resolution desired, which is a function of the frequency of the microwaves, and the index of refraction of the specimen. When a transducer with multiple detectors is used (rather than a single detector), then the number of scans may be reduced, as multiple images optimized at different depths may be created with data from a single scan.

The power supply for the microwave generator comprised a regulated, low-voltage power supply between 5 and 12 VDC, capable of supplying current sufficient to drive the Gunn diode. The 5-12 volts were delivered to the transducer housing, where power was delivered to the transducer. The same power supply was configured to provide the required voltages for the amplifiers, position encoders, and data acquisition system. Power for the data acquisition system could also be provided by the notebook computer via the USB interface.

Signal Analysis and Determination of Thickness

The novel technique is based, in part, on the principle that interfaces between materials with different dielectric constants (including, for example, overall thickness changes) act as microwave reflectors. When a scan is made by measuring the SIGNAL at different X and Y positions, and the data are used to create an image, these thickness changes can be displayed directly (as in a thickness map of the specimen).

During scanning with the prototype device, information was simultaneously gathered for values of the two SIGNAL channels, the X location, and the Y location. These data were processed by computer to produce a two-dimensional image of the SIGNAL.

Obstacles Overcome by the Present Invention.

Figure 1:
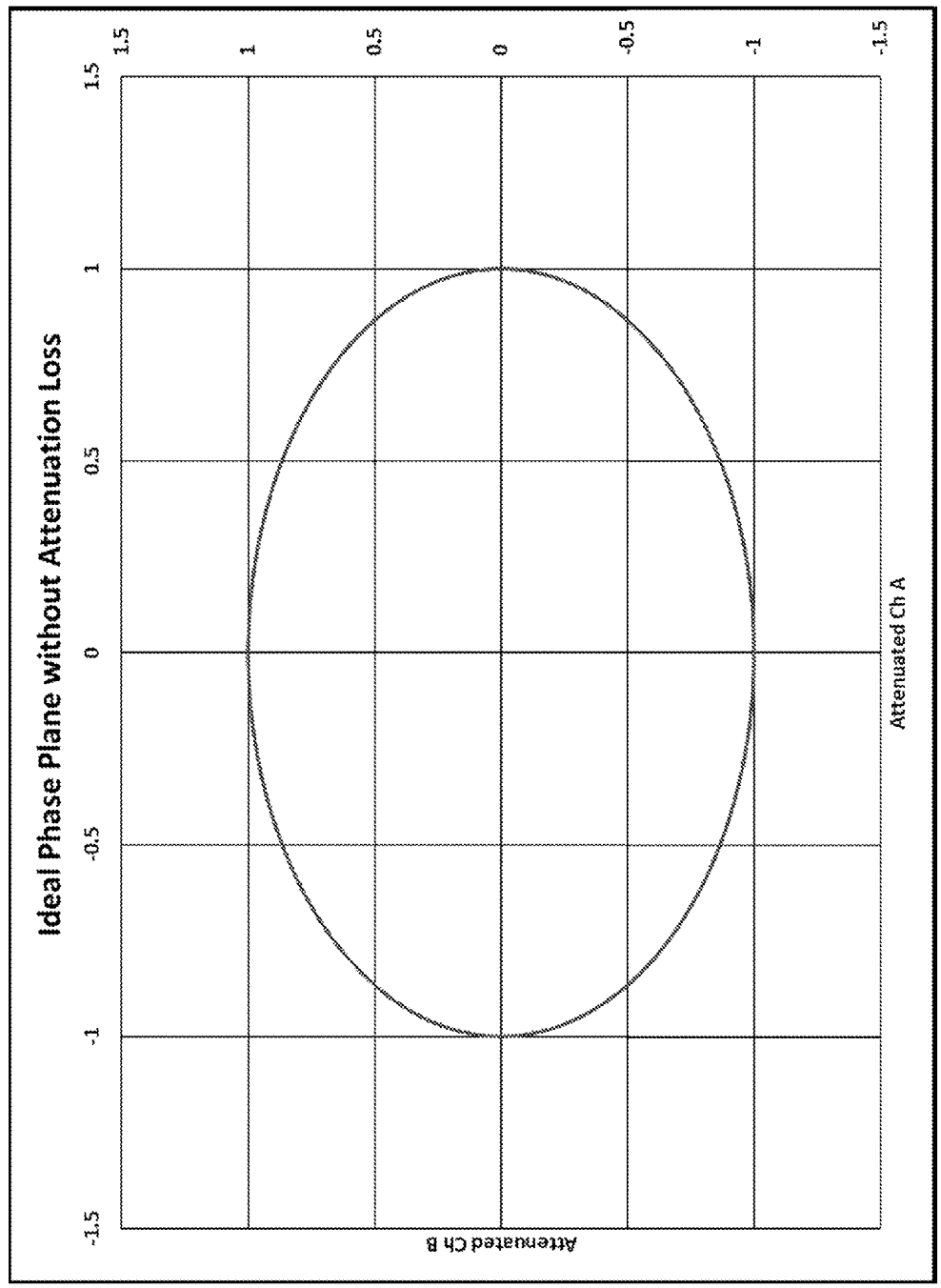
FIG. 1 depicts a phase plane plot showing detector A and B output voltages as (X,Y) data pairs in two dimensions, for a case with two detectors and a detector spacing of λ/4. This plot is for a hypothetical, idealized case in which no attenuation in the material occurs.
Figure 2:
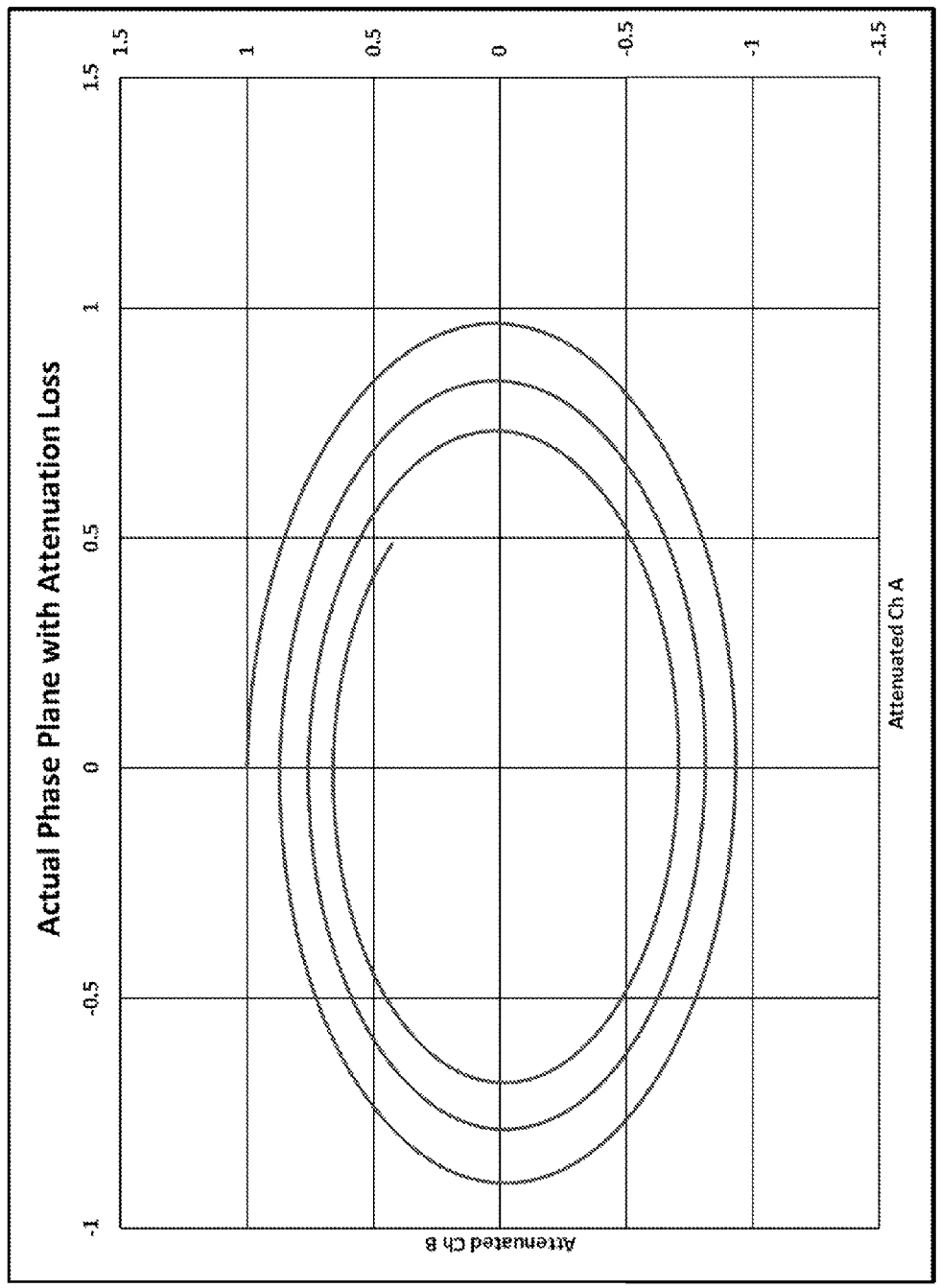
FIG. 2 depicts a phase plane plot showing detector A and B output voltages as (X,Y) data pairs in two dimensions, for a case with two detectors and a detector spacing of λ/4. This plot is also for a hypothetical, idealized case, but it represents a more realistic system in which microwave energy is lost in the inspected material by attenuation (as a function of what is often termed the "loss tangent" of the material).
Figure 3:
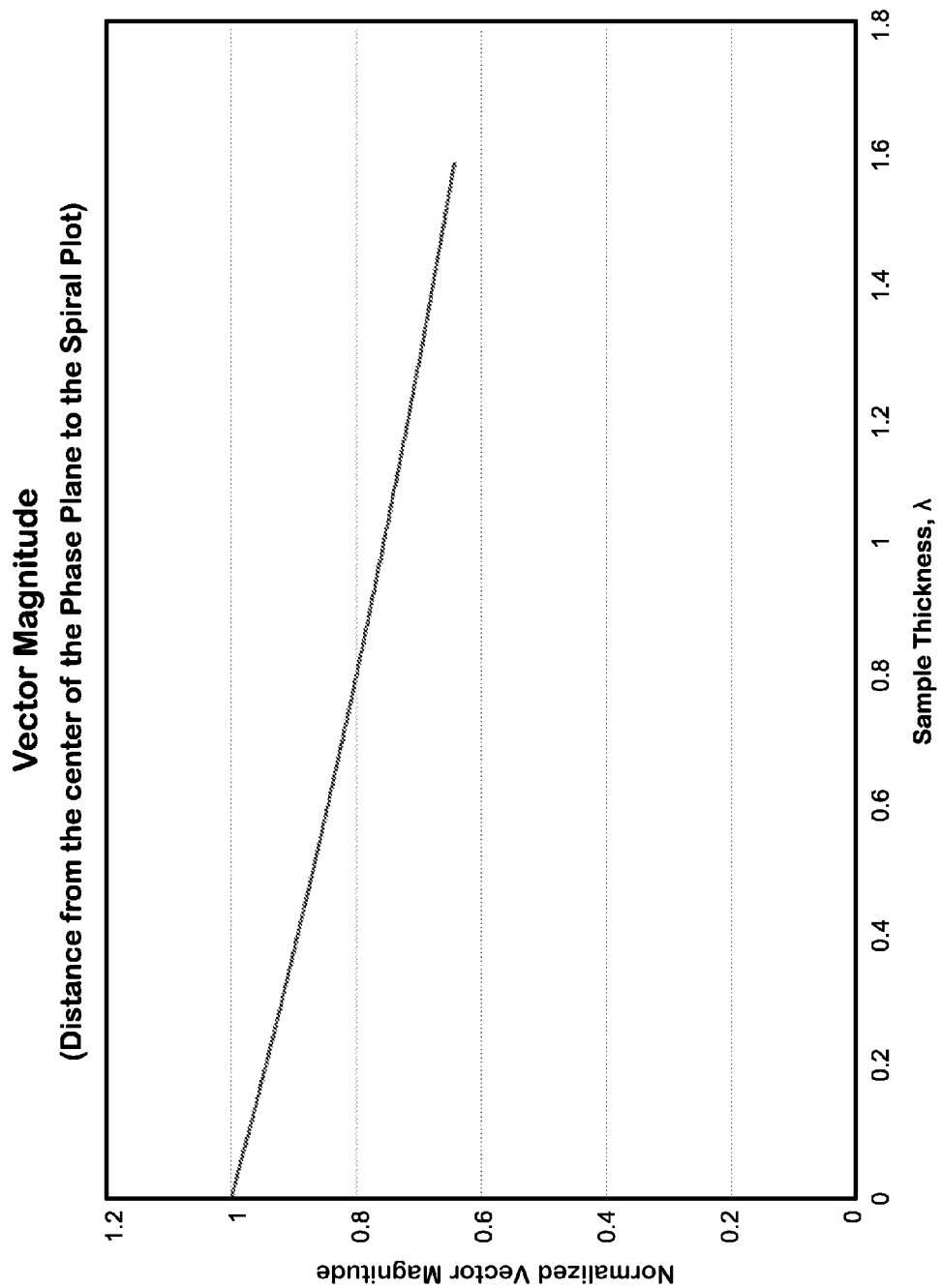
FIG. 3 depicts schematically the distance from the Phase Plane spiral to its center as a function of sample thickness.
Figure 4:
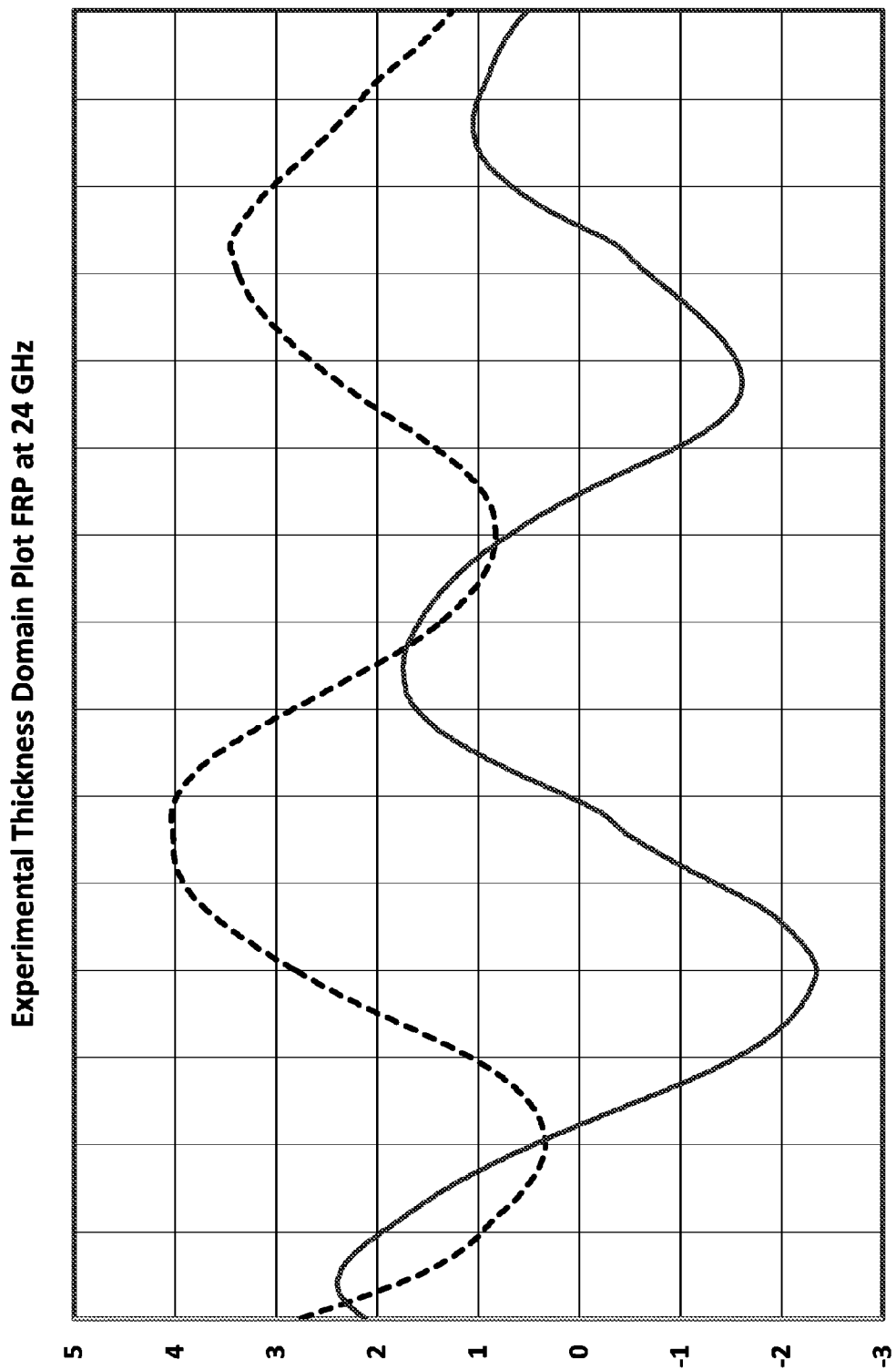
FIG. 4 depicts an experimentally measured thickness domain plot using two detectors.
Figure 5:
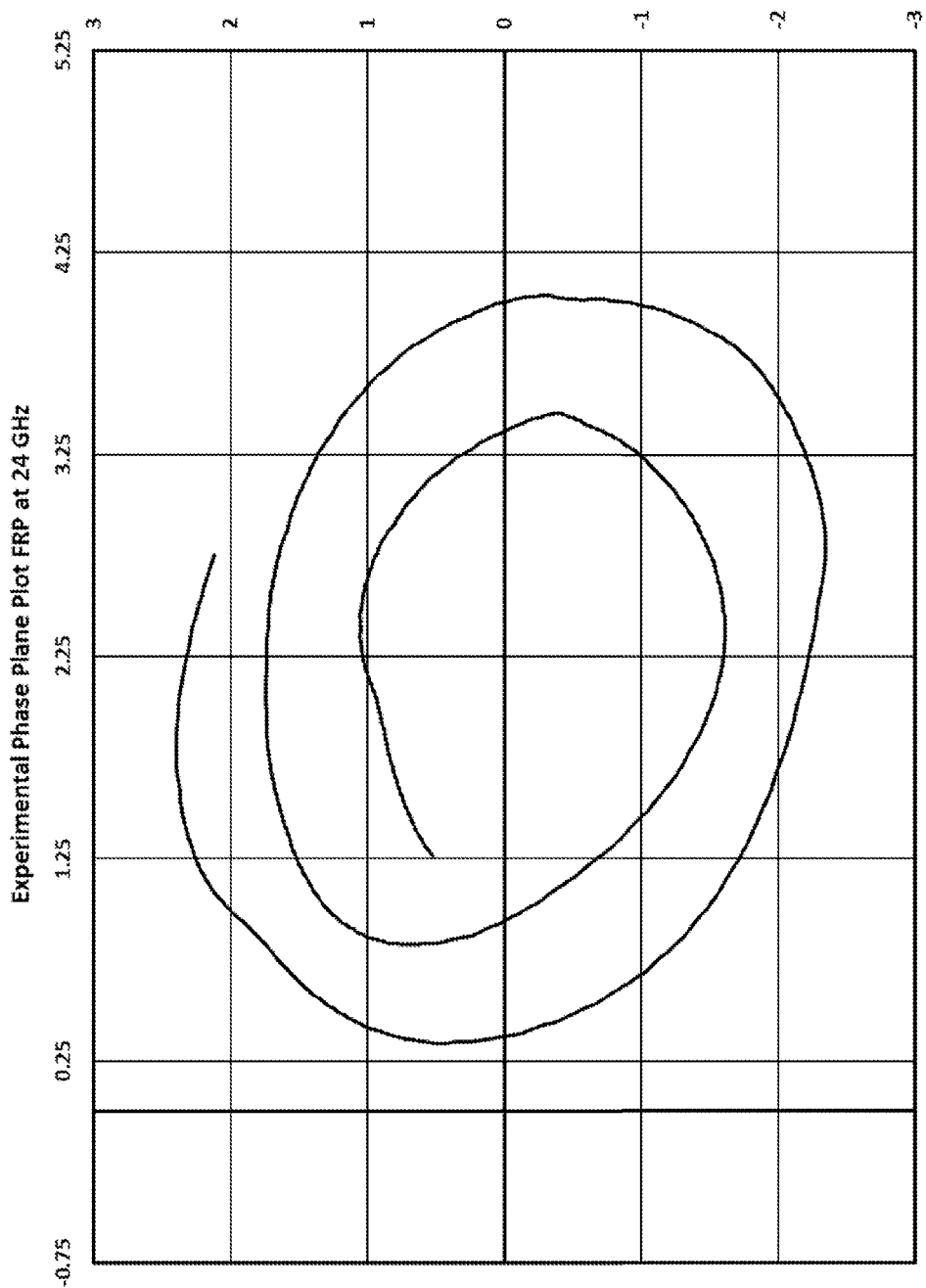
FIG. 5 depicts an experimentally measured phase plane plot.

The distance from a point on the Phase Plane spiral to its center, termed the "vector magnitude," changes more-or-less exponentially with thickness (becoming longer at lower thicknesses, and shorter at higher thicknesses—see FIG. 3). This ideal exponential behavior occurs when the effective channel gains are identical and the effective phase difference between the two detectors is precisely $\lambda/4$ ($\lambda$ in air). Since a combination of vector magnitude and phase angle is used to determine thickness unambiguously, ideally the transducer is positioned so that the effective phase angle between detectors is $\lambda/4$.

If the microwave propagation could indeed be described accurately as a simple plane wave propagation, then the optimum distance between the two detectors (in the direction of propagation) would simply be $\lambda/4$. However, when an actual transducer was built with a simple $\lambda/4$ displacement between the detectors and tested, the observed results were not as expected. The propagation of microwaves inside a finite transducer is in fact neither an idealized spherical wave front, nor an idealized planar wave front, but instead is a complex hybrid between these two idealized cases. As a result, the optimum distance between the detectors is not simply $\lambda/4$, as one might initially expect. Instead, the optimum distance may be empirically determined for a particular wavelength and a particular waveguide. When the detectors are optimally positioned, the vector magnitude varies approximately exponentially with the thickness, and does not oscillate substantially as the thickness changes.

An additional complication is that the Phase Plane plot is truly symmetric only when the effective gains used to amplify the signals from all detectors are equal. However, unlike for the case for incorrect physical placement of the detectors, when different gains are used the unequal gain ratios can be corrected in post-processing.

With previous microwave inspection techniques, it has sometimes been necessary to adjust the "null" or offset voltage of a detector signal to prevent signal saturation and clipping. When the null voltage is changed for either or both detectors, the center of the phase plane plot will move as well. This complication has made it difficult or impossible to determine thickness unambiguously using prior microwave inspection techniques, because for any real sample only a very small portion of the phase plane spiral is available. (Indeed, if the thickness does not change, only a single point is known.) If the location of the center is not known, then the vector magnitude cannot be calculated and the thickness cannot be determined. By contrast, in the current invention the null or offset voltages are preferably maintained constant, so that the center of the phase plane spiral is known, and the vector magnitude and thickness can be determined unambiguously.

A preferred method for practicing the invention is to plot points in phase plane space as described above, and to correlate those points with unique distances empirically. However, those of skill in the art will recognize that other methods of achieving the same result are mathematically equivalent to the preferred method. For purposes of the present specification and claims, any mathematically equivalent method is considered to be identical to the preferred method, and to be within the scope of the invention as defined.

The complete disclosures of all references cited in this specification, including priority application 61/882,288 and the Appendix to the priority application, are hereby incorporated by reference. In the event of an otherwise irreconcilable conflict, however, the present specification shall control.

What is claimed:

1. A method for nondestructively and unambiguously measuring the thickness of a bulk dielectric material, or measuring the depth of a feature in a bulk dielectric material, or both; said method comprising the steps of:

(a) generating microwaves from a microwave source, wherein the microwaves have substantially constant frequency;
(b) directing a first portion of the generated microwaves to the material to produce a standing wave; wherein the standing wave is a function of the wavelength of the microwaves, of the distance from the source to the nearest surface of the material, and of the distance from the source to farthest surface of the material or the distance from the source to a feature within the material;
(c) mixing the reflected microwaves, in each of at least two different detectors, with a second portion of the generated microwaves to produce an interference signal for each of the detectors; wherein the detectors are spatially displaced from one another; wherein the interference signal is a function of the thickness of the material, or a function of the depth of a feature within the material, or both; and wherein there is a phase difference between the different detectors at the frequency of the microwaves as a consequence of the spatial displacement between the detectors;
(d) determining, for each of one or more locations on or in the material, a point in a phase plane space whose coordinates correspond to the magnitude and sign of the interference signals that are produced at each of the detectors for each of the one or more locations; and
(e) correlating, for each of the one or more locations on or in the material, the point that is determined in the phase plane space with a unique thickness for the material at each location, or with a unique depth for a feature within the material, or both.

2. The method of claim 1, wherein said method is used to measure the thickness of the material.

3. The method of claim 1, wherein said method is used to measure the depth of a feature in the material.

4. A method comprising repeating the steps of claim 1 for a plurality of locations on or in the material, and forming an image that displays graphically the changes in thickness, or that displays graphically the depths of features, or both for each of the plurality of locations; whereby the image visually depicts the thickness of the material, or the locations of features within the material, or both.

5. The method of claim 4, wherein the image is two-dimensional.

6. The method of claim 4, wherein the image is three-dimensional.

7. The method of claim 4, wherein the image is three-dimensional, and wherein the image additionally depicts a fourth dimension via changes in the color of the image, wherein variations in the color indicate the presence of defects in the material.

8. The method of claim 1, wherein the resolution of the thickness measurements, depth measurements, or both is substantially smaller than the wavelength of the microwaves.

9. The method of claim 1, wherein the material is a composite material.

10. The method of claim 1, wherein the phase difference between at least one pair of the detectors is about one-fourth the wavelength of the microwaves.

11. The method of claim 1, wherein said method is repeated at each of a plurality of different microwave frequencies, to enhance the resolution of discrimination between different substances that have differential responses to radiation as a function of microwave frequency.

12. An apparatus for nondestructively and unambiguously measuring the thickness of a bulk dielectric material, or measuring the depth of a feature in a bulk dielectric material, or both; said apparatus comprising:
(a) a generator of microwaves of substantially constant frequency; wherein said generator is adapted to direct a first portion of the generated microwaves to the material to create a standing wave; wherein the standing wave is a function of the wavelength of the microwaves, of the distance from the source to the nearest surface of the material, and of the distance from the source to farthest surface of the material or the distance from the source to a feature within the material;
(b) at least two different detectors displaced spatially from one another, wherein each of said detectors is adapted to add the reflected microwaves with a second portion of the generated microwaves to produce an interference pattern for each of said detectors; wherein the interference pattern is a function of the thickness of the material, or a function of the depth of a feature within the material, or both; wherein there is a phase difference between the different said detectors at the frequency of the microwaves as a consequence of the displacement between said detectors; and
(c) a computer programmed to determine, for one or more locations on or in the material, a point in a phase plane space whose coordinates correspond to the magnitude and sign of the interference signals that are produced at each of said detectors for the one or more locations; and to correlate, for each of the one or more locations, the point that is determined in the phase plane space with a unique thickness for the material at each location, or with a unique depth for the feature within the material, or both.

13. The apparatus of claim 12, wherein the computer is programmed to determine, for a plurality of locations on or in the material, the thickness of the material, or the depth of a feature in the material, or both; and to form an image that displays graphically the changes in thickness or that displays graphically the depths of features, or both for each of the plurality of locations, whereby the image visually depicts the thickness of the material, or the locations of features within the material, or both.

14. The apparatus of claim 13, wherein the image is two-dimensional.

15. The apparatus of claim 13, wherein the image is three-dimensional.

16. The apparatus of claim 13, wherein the image additionally depicts a fourth dimension of information via changes in the color of the image, wherein variations in the color indicate the presence of defects in the material.

17. The apparatus of claim 12, wherein said apparatus is adapted to measure thickness, feature depth, or both with a resolution that is substantially smaller than the wavelength of the microwaves.

18. The apparatus of claim 12, wherein the phase difference between at least one pair of said detectors is about one-fourth the wavelength of the microwaves.

19. The apparatus of claim 12, wherein said apparatus is programmed to repeat the thickness or depth measurements at each of a plurality of different microwave frequencies, to enhance the resolution of the discrimination between different substances that have differential responses to radiation as a function of microwave frequency.

* * * * *